United States Patent [19]

Jackson et al.

[11] Patent Number: 5,614,281

[45] Date of Patent: Mar. 25, 1997

[54] CREPED NONWOVEN LAMINATE LOOP FASTENING MATERIAL FOR MECHANICAL FASTENING SYSTEMS

[75] Inventors: Wanda W. Jackson, Alpharetta; Monica S. Diaz, Woodstock; Lance J. Garrett, Jr., Marietta, all of Ga.

[73] Assignee: Kimberly-Clark Corporation, Neenah, Wis.

[21] Appl. No.: 565,618

[22] Filed: Nov. 29, 1995

[51] Int. Cl.$^6$ .................................................. B32B 3/06
[52] U.S. Cl. ....................... 428/100; 24/450; 428/99; 428/152; 428/198; 428/218; 604/391
[58] Field of Search ..................... 428/198, 284, 428/286, 296, 297, 298, 152, 218, 99, 100; 604/391; 24/450

[56] References Cited

U.S. PATENT DOCUMENTS

| | | | |
|---|---|---|---|
| 4,205,679 | 6/1980 | Repke et al. | 128/287 |
| 4,487,796 | 12/1984 | Lloyd et al. | 428/154 |
| 4,973,326 | 11/1990 | Wood et al. | 604/391 |
| 4,994,054 | 2/1991 | Pigneul et al. | 604/391 |
| 5,407,439 | 4/1995 | Goulait | 604/391 |

FOREIGN PATENT DOCUMENTS

| | | |
|---|---|---|
| 0264676A1 | 4/1988 | European Pat. Off. . |
| 0409315A1 | 1/1991 | European Pat. Off. . |
| 94/08789 | 4/1994 | WIPO . |
| 94/28751 | 12/1994 | WIPO . |
| 95/07677 | 3/1995 | WIPO . |
| 95/12072 | 5/1995 | WIPO . |
| 95/25496 | 9/1995 | WIPO . |
| 95/33390 | 12/1995 | WIPO . |

Primary Examiner—James J. Bell
Attorney, Agent, or Firm—James B. Robinson; Nicholas N. Leach

[57] ABSTRACT

The creped nonwoven laminate loop material of the present invention includes a creped nonwoven layer attached to a support layer. The creped nonwoven layer may be, for example, a spunbond nonwoven web or a staple fiber bonded carded web. The support layer may be formed of any material that can be suitably attached or bonded to the creped nonwoven layer, including a foam, a plastic film or another nonwoven web. The exposed, top surface of the creped nonwoven layer includes raised "loop" areas having low fiber density and high z-directional fiber orientation that are designed to receive and engage the hook elements projecting from a hook material. The raised areas of the creped nonwoven layer are separated by non-raised areas having relatively higher fiber density and relatively lower z-directional fiber orientation when compared to the fiber density and z-directional fiber orientation of the raised areas. The primary areas of bonding or attachment of the bottom surface of the nonwoven layer to the top surface of the underlying support layer are the non-raised areas; in addition, some secondary bonding of the nonwoven layer to the support layer outside of the non-raised areas may exist. The support layer provides structural integrity for the creped nonwoven laminate material and dimensionally stabilizes the creped nonwoven layer. The creped structure of the nonwoven layer further provides resistance against compression of the fibers forming the hook receiving loop material during use, thereby facilitating entry and engagement of hook elements projecting from the hook material. The creped nonwoven loop laminate of this invention can be employed as the loop material of a hook and loop fastening system, such as used on disposable personal care absorbent articles.

20 Claims, 6 Drawing Sheets

CREPED NONWOVEN LAMINATE LOOP FASTENING MATERIAL FOR MECHANICAL FASTENING SYSTEMS

FIELD OF INVENTION

The present invention is directed to a loop fastening material for mechanical fastening systems, commonly referred to as hook and loop fastener systems. More specifically, this invention relates to a loop fastening material in the form of a nonwoven laminate having a creped nonwoven layer attached to a support layer for engaging the hooks of a complementary hook material.

BACKGROUND OF THE INVENTION

Mechanical fastening systems, of the type otherwise referred to as hook and loop fastener systems, have become increasingly widely used in various consumer and industrial applications. A few examples of such applications include disposable personal care absorbent articles, clothing, sporting goods equipment, and a wide variety of other miscellaneous articles. Typically, such hook and loop fastening systems are employed in situations where a refastenable connection between two or more materials or articles is desired. These mechanical fastening systems have in many cases replaced other conventional devices used for making such refastenable connections, such as buttons, buckles, zippers, and the like.

Mechanical fastening systems typically employ two components—a male (hook) component and a female (loop) component. The hook component usually includes a plurality of semi-rigid, hook-shaped elements anchored or connected to a base material. The loop component generally includes a resilient backing material from which a plurality of upstanding loops project. The hook-shaped elements of the hook component are designed to engage the loops of the loop material, thereby forming mechanical bonds between the hook and loop elements of the two components. These mechanical bonds function to prevent separation of the respective components during normal use. Such mechanical fastening systems are designed to avoid separation of the hook and loop components by application of a shear force or stress, which is applied in a plane parallel to or defined by the connected surfaces of the hook and loop components, as well as certain peel forces or stresses. However, application of a peeling force in a direction generally perpendicular or normal to the plane defined by the connected surfaces of the hook and loop components can cause separation of the hook elements from the loop elements, for example, by breaking the loop elements and thereby releasing the engaged hook elements, or by bending the resilient hook elements until the hook elements disengage the loop elements.

Mechanical fastening systems can be advantageously employed in disposable personal care absorbent articles, such as disposable diapers, disposable garments, disposable incontinence products, and the like. Such disposable products generally are single-use items which are discarded after a relatively short period of use—usually a period of hours—and are not intended to be washed and reused. As a result, it is desirable to avoid expensive components in the design of such products. Thus, to the extent that the hook and loop components are employed in such products, the hook and loop components need to be relatively inexpensive in terms of both the materials used and the manufacturing processes for making these components. On the other hand, the hook and loop components must have sufficient structural integrity and resiliency to withstand the forces applied thereto during normal wear of the absorbent article, in order to avoid potentially embarrassing situations for the wearer that can result from premature separation or disengagement of the hook and loop components.

U.S. Pat. No. 4,761,318 to Ott et al. discloses a loop fastening material useful in a mechanical fastening system for disposable articles. The loop fastening material disclosed by this patent includes a fibrous layer having a plurality of loops on a first surface adapted to be releasably engaged by a mating hook fastener portion and a layer of thermoplastic resin adhered to a second surface of the fibrous structure opposite the first surface. The thermoplastic resin anchors the loops in the fibrous structure.

U.S. Pat. No. 5,032,122 to Noel et al. discloses a loop fastening material useful in a mechanical fastening system for a disposable article. The loop fastening material disclosed by this patent includes a backing of orientable material and a multiplicity of fibrous elements extending from the backing. The fibrous elements are formed by continuous filaments positioned on and intermittently secured to the backing when the orientable material of the backing is in its dimensionally unstable state. The fibrous elements are formed by the shirring of the filaments between spaced, fixed regions of securement to the backing when the orientable material is caused to be transformed to its dimensionally stable state such that it is caused to contract or gather along its path of response. Thus, the loop material of this patent requires a backing of orientable material, such as an elastic or elastomeric or heat shrinkable material, that is caused to be transformed from a dimensionally stable state to a dimensionally unstable state and returned it to its dimensionally stable state.

U.S. Pat. No. 5,326,612 to Goulait discloses another a loop fastening material useful in a mechanical fastening system for a disposable article. The loop fastening material disclosed by this patent includes a nonwoven web secured to a backing. The nonwoven web serves to admit and entangle the hooks of a complementary hook component. The nonwoven web has a specified basis weight range of between about 5 to about 42 $g/m^2$, an inter-fiber bond area of less than about 10 percent, and a total plan view bonded area of less than about 35 percent.

Notwithstanding the teachings of the aforementioned references, the need nonetheless exists for an improved loop fastening material for a mechanical fastening system, particularly as such are used in disposable personal care absorbent articles. The creped nonwoven laminate loop fastening material of the present invention is soft and cloth-like, and therefore, aesthetically appealing in terms of appearance and feel. The loop material of the present invention is relatively inexpensive to produce, especially in comparison to conventional loop materials formed by knitting, warp knitting, weaving, and the like, yet exhibits comparable and/or improved peel and shear strengths as compared to conventional loop fastening materials when used with commercially available hook fastener materials.

SUMMARY OF THE INVENTION

The present invention is directed to an improved loop fastening material for hook and loop fastening systems. The loop material of this invention has a three-dimensional surface topography particularly suitable for receiving and engaging hook elements of a complementary hook material. The hook material can be any of a wide variety of commercially available hook components which, as is known in the art, typically include a base material from which a plurality of hook elements project.

The creped nonwoven laminate loop material of the present invention includes a creped nonwoven layer attached to a support layer. The creped nonwoven layer may be, for example, a spunbond nonwoven web or a staple fiber bonded carded web. The support layer may be formed of any material that can be suitably attached or bonded to the creped nonwoven layer, including a plastic film or another nonwoven web. The exposed, top surface of the creped nonwoven layer includes raised "loop" areas having low fiber density and high z-directional fiber orientation that are designed to receive and engage the hook elements projecting from a hook material. The raised areas of the creped nonwoven layer are separated by non-raised areas having relatively higher fiber density and relatively lower z-directional fiber orientation when compared to the fiber density and z-directional fiber orientation of the raised areas. The primary areas of bonding or attachment of the fibers or filaments forming the nonwoven layer to the top surface of the underlying support layer are the non-raised areas; in addition, some secondary bonding of the fibers or filaments of the nonwoven layer to the support layer outside of the non-raised areas may exist. The support layer provides structural integrity for the creped nonwoven laminate material and dimensionally stabilizes the creped nonwoven layer. The creped structure of the nonwoven layer further provides resistance against compression of the fibers forming the hook receiving loop material during use, thereby facilitating entry and engagement of hook elements projecting from the hook material. The creped nonwoven loop laminate of this invention can be employed as the loop material of a hook and loop fastening system, such as used on disposable personal care absorbent articles.

A suitable process for forming the creped nonwoven laminate loop material of this invention includes: providing a nonwoven layer, providing a support layer, providing opposedly positioned first and second heated calender rolls defining a nip therebetween, said first roll having a patterned outermost surface and said second roll having a flat outermost surface, rotating said first and second rolls in opposite directions, said first roll having a first rotational speed and said second roll having a second rotational speed, said second rotational speed being 2 to 8 times greater than said first rotational speed, and passing the nonwoven layer and support layer within the nip formed by said first and second counter-rotating rolls to form a creped nonwoven laminate. As a result of this forming process, the basis weight of the nonwoven layer is increased from a first basis weight prior to being creped and laminated to a second, higher basis weight after it exits the nip formed by the counter-rotating pattern and anvil rolls.

When used as the loop component of a hook and loop fastening system for a disposable personal care absorbent article, the creped nonwoven laminate loop material of this invention can be bonded or attached to the outer layer or backsheet of the article as a discrete patch of loop material. Alternatively, the creped nonwoven laminate loop material can form the entire outer cover or backsheet of such a disposable personal care absorbent article.

DETAILED DESCRIPTION OF THE INVENTION

The present invention relates to an improved loop fastening material for a mechanical or hook and loop fastening system. For purposes of illustration only, the present invention will be described separately and in conjunction with its use with disposable personal care absorbent articles, which include diapers, training pants, incontinence garments, sanitary napkins, bandages and the like. As such, the invention should not be limited to these specific uses, as it is instead intended that the present invention be used in all applications in which hook and loop fasteners can be employed.

The loop material of the present invention is intended to be utilized with a wide variety of hook materials. Exemplary of hook materials suitable for use with the loop material of the present invention are those obtained from: Velcro Group Company, of Manchester, N.H., under the trade designations CFM-22-1097; CFM-22-1121; CFM-22-1162; CFM-25-1003; CFM-29-1003; and CFM-29-1005; or Minnesota Mining & Manufacturing Co., of St. Paul, Minn., under the designation CS 200. Suitable hook materials generally comprise from about 16 to about 620 hooks per square centimeter, or from about 124 to about 388 hooks per square centimeter, or from about 155 to about 310 hooks per square centimeter. The hooks suitably have a height of from about 0.00254 centimeter (cm) to about 0.19 centimeter, or from about 0.0381 centimeter to about 0.0762 centimeter.

Figure 3:
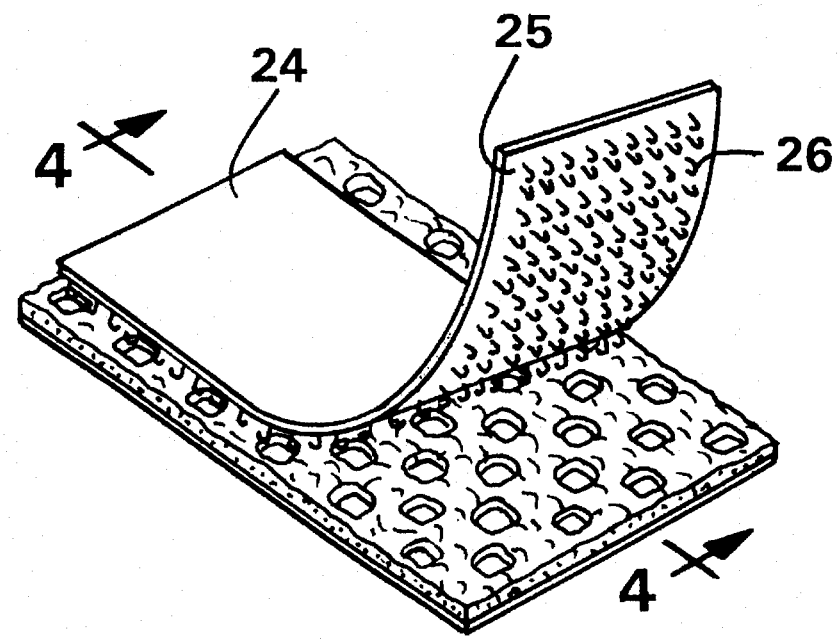
FIG. 3 is a perspective view of a hook material engaged with the loop material of FIG. 1.
Figure 4:
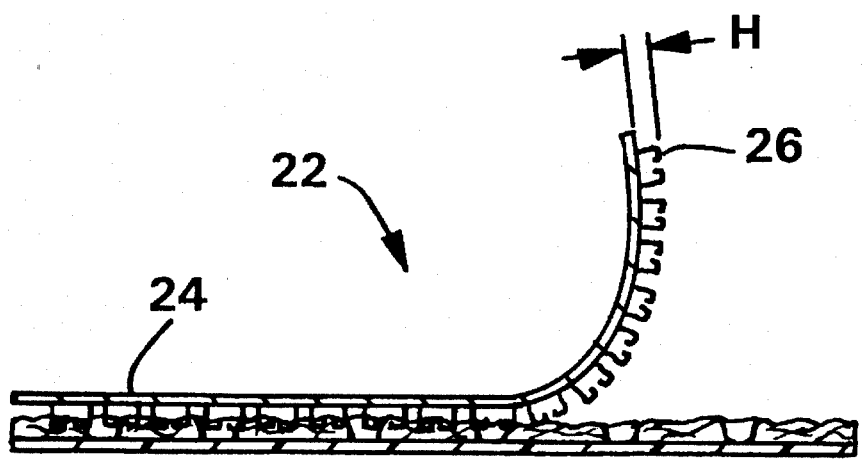
FIG. 4 is a cross-sectional side view of the hook and loop materials shown in FIG. 3.

As can be seen in FIGS. 3 and 4, the hook material 22 includes a base layer 24 with a plurality of bi-directional hook elements 26 extending generally perpendicularly therefrom. As used herein, the term "bi-directional" refers to a hook material having individual adjacent hook elements oriented in opposite directions in the machine direction of the hook material. The term "uni-directional," on the other hand, refers to a hook material having individual adjacent hook elements oriented in the same direction in the machine direction of the hook material.

In order to achieve constant data regarding the present invention, a single type of hook material was used in evaluating the loop material of the present invention. The hook elements 26 have an average overall height H measured from the top surface 25 of the base material 24 to the highest point on the hook elements 26. The average height of the hook elements 26 used in conjunction with the present invention is about 0.5 millimeter (mm). Hook material 22 has a hook density of about 265 hooks per square centimeter. The thickness of base material 24 is about 3.5 mils. The hook material 22 used in conjunction with the present invention is available from Velcro USA as CFM-29-1003. Other dimensions and properties of the hook material 22 are as outlined in the examples described hereinbelow.

Although the term "hook material" is used herein to designate the portion of a mechanical fastening system having engaging (hook) elements, it is not intended to limit the form of the engaging elements to only include "hooks" but shall encompass any form or shape of engaging element, whether uni-directional or bi-directional, as is known in the art to be designed or adapted to engage a complementary loop fastening material, such as the creped nonwoven laminate loop material of the present invention.

Figure 1:
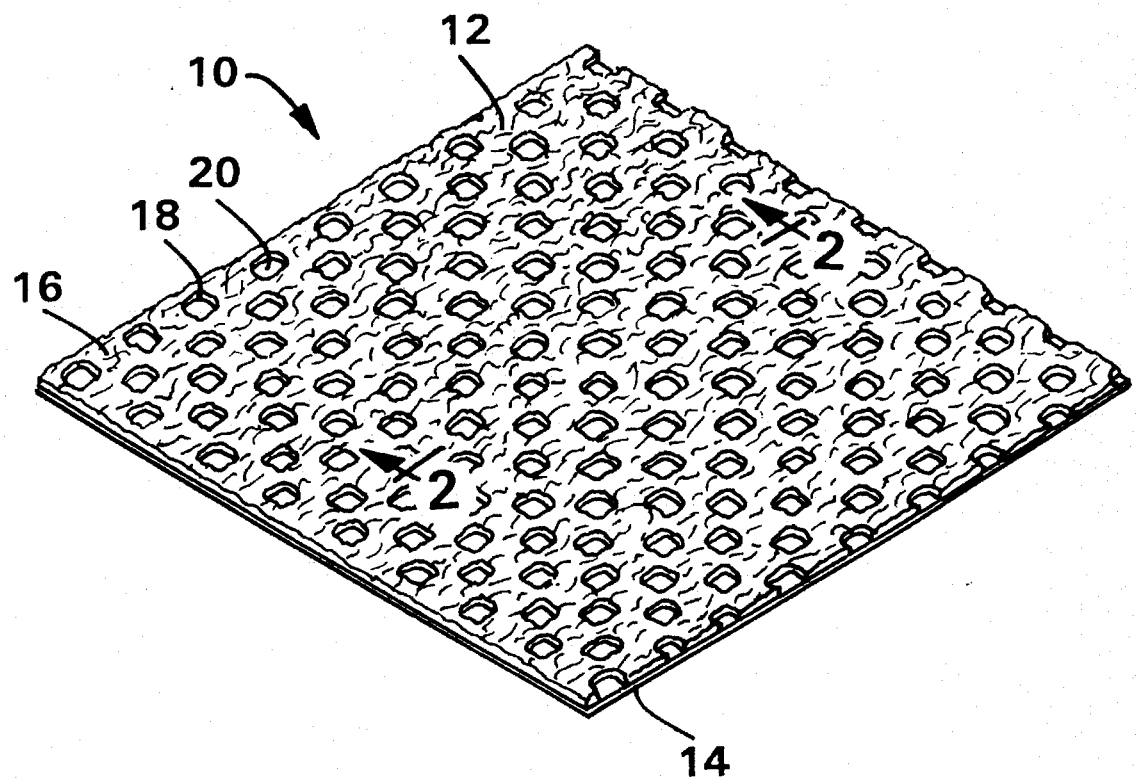
FIG. 1 is a perspective view of the loop material of the present invention.
Figure 2:
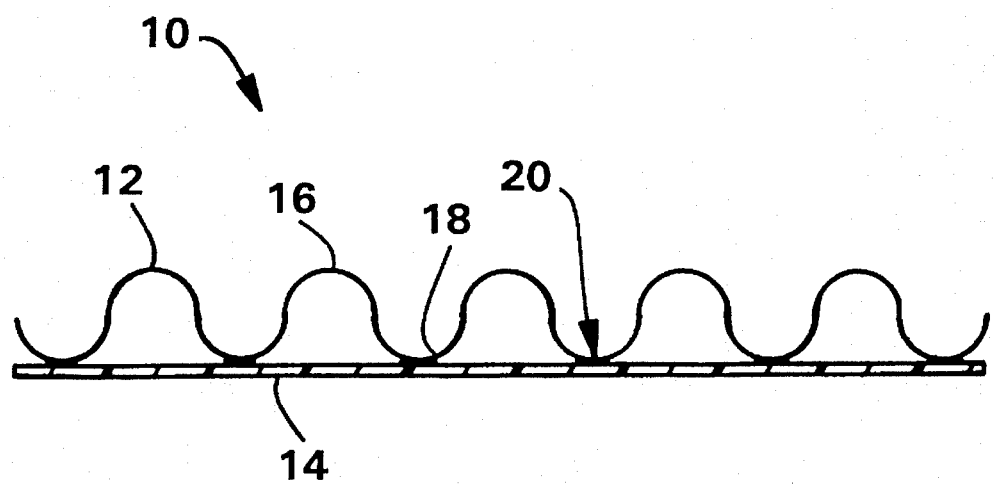
FIG. 2 is a cross-sectional side view of the loop material of FIG. 1.

Referring to FIGS. 1 and 2, an embodiment of the creped nonwoven laminate loop material 10 of the present invention is illustrated. By way of definition, the term "creped nonwoven laminate loop material" as used herein is intended to refer to a loop or female component for a hook and loop fastening system that comprises, in its simplest form, a creped nonwoven layer or web secured to a support layer or web. This term is not intended to limit the loop material of the present invention to only nonwoven materials; rather, the loop material of the present invention also includes alternative embodiments in which, for example, the support layer or web is not a nonwoven layer or web, as will described hereinbelow. Nor is use of the term "loop" intended to limit the loop material of the present invention to only materials in which discrete, separately formed loops of material are employed to receive and engage the hook elements of a complementary hook material; rather, the loop material of the present invention includes fibrous nonwoven layers in which the individual fibers function to engage the hook elements without such fibers being formed into discrete loops.

As used herein, the terms "layer" or "web" when used in the singular can have the dual meaning of a single element or a plurality of elements. As used herein, the term "laminate" means a composite material made from two or more layers or webs of material which have been attached or bonded to one another.

Referring again to FIGS. 1 and 2, loop material 10 is shown comprising a creped nonwoven layer 12 bonded to a support layer 14. Nonwoven layer 12 can be generally described as any nonwoven web that, when formed in accordance with the present invention, is suitable for receiving and engaging the hooks of a complementary hook material. As used herein, the terms "nonwoven layer" or "nonwoven web" mean a web having a structure of individual fibers or threads which are interlaid, but not in an identifiable manner as in a knitted fabric. Commercially available thermoplastic polymeric materials can be advantageously employed in making the fibers or filaments from which nonwoven layer 12 is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specifically limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers of the foregoing. The fibers used in making nonwoven layer 12 may have any suitable morphology and may include hollow or solid fibers, straight or crimped fibers, bicomponent, multicomponent, biconstituent or multiconstituent fibers, and blends or mixes of such fibers, as are well known in the art.

Nonwoven webs that can be employed as nonwoven layer 12 of the present invention can be formed by a variety of known forming processes, including spunbonding, airlaying, or bonded carded web formation processes. Spunbond nonwoven webs are made from melt-spun filaments. As used herein, the term "melt-spun filaments" refers to small diameter fibers and/or filaments which are formed by extruding a molten thermoplastic material as filaments from a plurality of fine, usually circular, capillaries of a spinnerette with the diameter of the extruded filaments then being rapidly reduced, for example, by non-eductive or eductive fluid-drawing or other well known spunbonding mechanisms. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dobo et al., all of which are incorporated herein by reference. The melt-spun filaments formed by the spunbond process are generally continuous and have diameters larger than 7 microns, more particularly, between about 10 and 20 microns.

In making the specific embodiment of the present invention shown in FIGS. 1 and 2, a conventional spunbond process may be used to form a nonwoven web of melt-spun filaments formed from an extrudable thermoplastic resin which is a random copolymer of propylene and ethylene. A random copolymer containing from about 0.5 to about 10 percent, by weight, ethylene and from about 99.5 to about 90 percent, by weight, propylene has been found to work well in the present invention.

Figure 9:
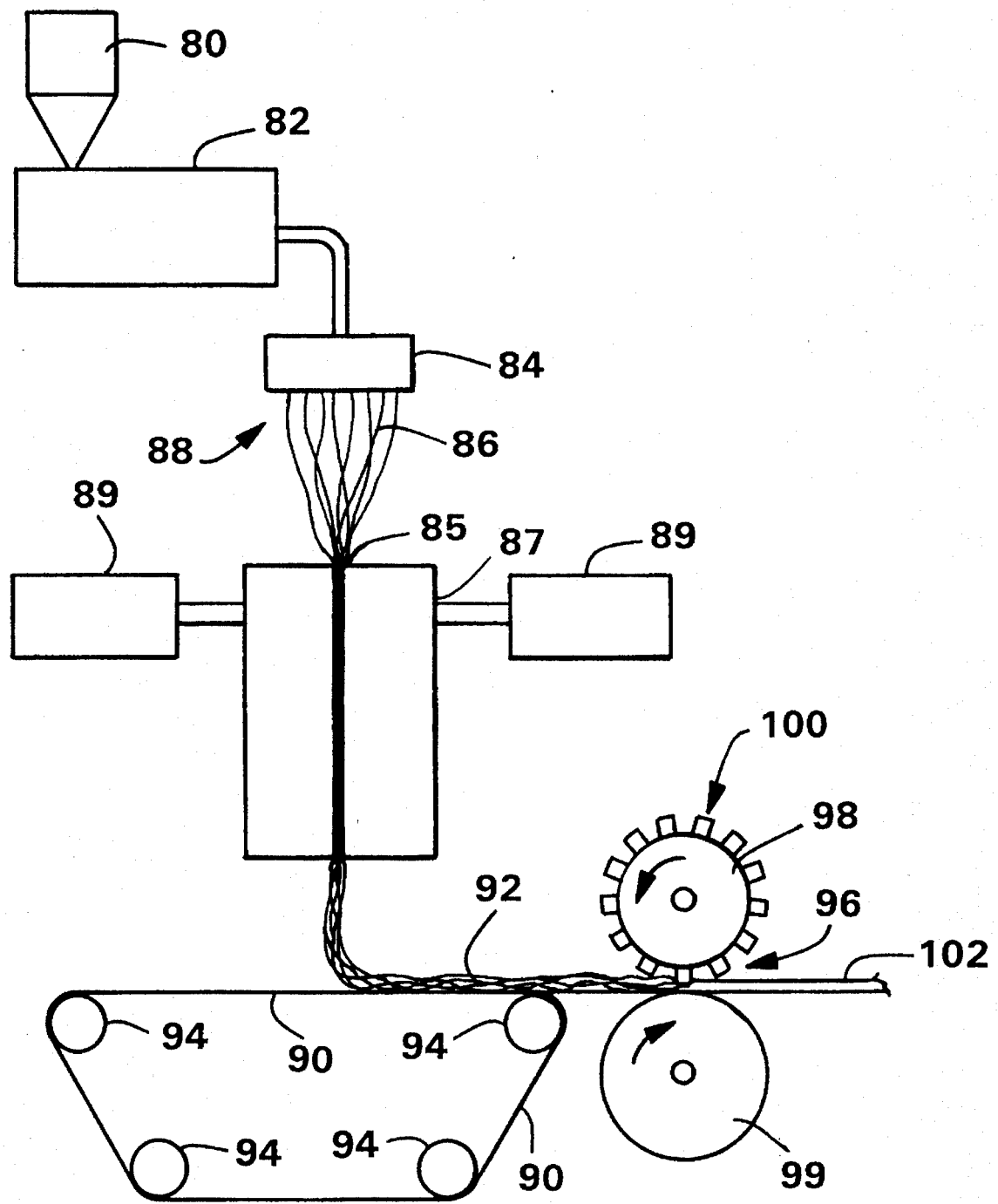
FIG. 9 is a schematic side view of an exemplary process and apparatus for producing a nonwoven web of spunbonded filaments.

A suitable spunbond process and apparatus for producing a nonwoven web of melt-spun copolymer filaments are schematically illustrated in FIG. 9. In forming such a spunbond web of melt-spun copolymer filaments (e.g., spunbonded filaments), pellets, chips or the like of a copolymer material are introduced into a pellet hopper 80 of an extruder 82. The extruder 82 has an extrusion screw (not shown) that is driven by a conventional drive motor (not shown). As the copolymer advances through the extruder 82, due to rotation of the extrusion screw by the drive motor, the copolymer is progressively heated to a molten state. Heating of the copolymer to the molten state may be accomplished in a plurality of discrete steps with its temperature being gradually elevated as it advances through discrete heating zones of the extruder 82 toward an extrusion die 84. The die 84 may be yet another heating zone where the temperature of the copolymer is maintained at an elevated level for extrusion. The temperature which will be required to heat the copolymer to a molten state will vary somewhat depending upon the type of copolymer used. For example, a random block copolymer containing about 3.2 percent, by weight, ethylene and about 96.8 percent, by weight, propylene, may be extruded at a temperature of from about 227° C. to about 260° C. Heating of the various zones of the extruder 82 and the extrusion die 84 may be achieved by any of a variety of conventional heating arrangements (not shown).

The filaments of the molten copolymer are initially formed and discharged in a stream 86 from spaced-apart filament forming means 88. The forming means 88 may be any suitable filament forming means, such as spinnerettes, die orifices, or similar equipment associated with melt-spinning processes such as, for example, the spunbonding process. The melt-spun filaments discharged from the forming means 88 are drawn through passage 85 in fiber draw unit 87, to which high speed fluid sources 89, such as jet streams of air, are operatively connected. The action of the high speed fluid on the melt-spun filaments 86 passing downwardly through passage 85 stretches the melt-spun filaments 86, and increases the speed of delivery of the melt-spun filaments to a forming surface. The melt-spun filaments upon exiting passage 85 are deposited in a random manner on a foraminous forming surface 90, generally assisted by a vacuum device (not shown) placed underneath the forming surface 90. The melt-spun filaments are between 1.5 and 5.0 denier per filament (dpf), and more particularly between 2.0 and 2.5 dpf. The purpose of the vacuum is to eliminate the undesirable scattering of the filaments and to guide the filaments onto the forming surface 90 to form a nonwoven web 92 of melt-spun copolymer filaments. The forming surface 90 is supported in turn on roller 94 driven by conventional drive means (not shown).

The nonwoven web 92 separates from the forming surface 90, and is directed into and through nip 96 of a patterned roller arrangement 100. The pattern roll 98 is used for thermal bonding of the web 92. The smooth anvil roll 99, together with the pattern roll 98, defines a thermal pattern bonding nip 96. Alternatively, anvil roll 99 also may bear a bonding pattern on its outer surface. The pattern roll 98 is heated to a suitable bonding temperature by heating means (not shown) and is rotated by conventional drive means (not shown), so that when the web 92 passes through nip 96, a series of thermal pattern bonds is formed. Nip pressure within nip 96 should be sufficient to achieve the desired degree of bonding of web 92, given the line speed, bonding temperature and materials forming web 92. For example, nip pressures within the range of about 60 to 85 pounds per lineal inch (pli) (about 1.07 to 1.51 kilograms per lineal millimeter) are suitable. As a result of the thermal pattern bonding, the web 92 of filaments becomes a pattern bonded web 102 of enhanced stability.

The percent bond area of the pattern bonded web 102 is important to the functionality of the creped nonwoven laminate loop material of this invention. Generally speaking, the percent bond area of the nonwoven web should be sufficiently high so that a majority of the generally continuous melt-spun filaments have portions that extend through at least two pattern bonds. In this way, individual filaments within the nonwoven web can more securely engage the hook elements of a hook material, resulting in suitable peel and shear strength properties for the loop material. In addition, a sufficiently high percent bond area serves to reduce fiber pull-out, which can result from repeated disengagement of hook elements from the loop material. A high incidence of fiber pull-out can reduce the peel and/or shear strength of the loop material, and deleteriously affect the appearance (i.e., increased fuzziness) of the loop material. Thus, increasing the percent bond area tends to improve the surface integrity and durability of the loop material. On the other hand, the percent bond area should not be so high that the number and size of inter-filament areas in which the hook elements of the hook material are received when engaging the loop material are insufficiently large to allow a sufficient number of hook elements to be received into the loop material. For example, in the spunbond apparatus illustrated in FIG. 9, the pattern roll 98 has a point bond pattern with a surface bond area between about 10 percent and about 25 percent or more, using a bond point density of between about 15.5 and 46.5 bond points per square centimeter. Alternatively, a pattern roll 98 having a surface bond area within the range of about 13 percent to about 22 percent, or within the range of about 15 percent to about 20 percent, has been found suitable for use in the present invention. Bond densities above and below the above-stated range also can be used, with the specific bond density being dependent upon the size of the individual bond points. The pattern bonded web 102 then is passed to other process and/or treatment steps.

Nonwoven layer 12 also may be made from bonded carded webs. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

Through-air bonders are well known in the art and need not be described in detail herein. Generally, a common type of through-air bonder includes a perforated roller, which receives the web, and a hood surrounding the perforated roller. A flow of heated air is directed from the hood and applied through the web and into the perforated roller. The heated air heats the web to a temperature above the melting point of the lower melting point component of the bicomponent filaments, but below the melting point of the higher melting point component. Upon heating, the lower melting polymer portions of the web filaments melt and adhere to adjacent filaments at their cross-over points, while the higher melting polymer portions of the filaments tend to maintain the physical and dimensional integrity of the web. For example, when polypropylene and polyethylene are used as the polymer components, the air flowing through the through-air bonder can have a temperature ranging from about 110° C. to about 140° C. and a velocity from about 30 to about 150 meters per minute. The dwell time of the web in the through-air bonder typically should not exceed about 6 seconds. It should be understood, however, that the parameters of the through-air bonder depend on factors such as the type of polymers used, the thickness of the web, etc.

Airlaying is another well known process by which fibrous nonwoven layer 12 can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

In order to obtain the specified range of physical properties in the resultant creped nonwoven layer 12 in accordance with the present invention, the bonding process used to bond the fibers or filaments of the nonwoven layer should be a process that can control the level of compression or collapse of the fibrous structure during the formation process. Whatever forming process is utilized, the degree of bonding will be dependent upon the fibers/polymers used, but in any event, it is desirable that the amount of web compression be controlled during the heating stage.

Figure 5:
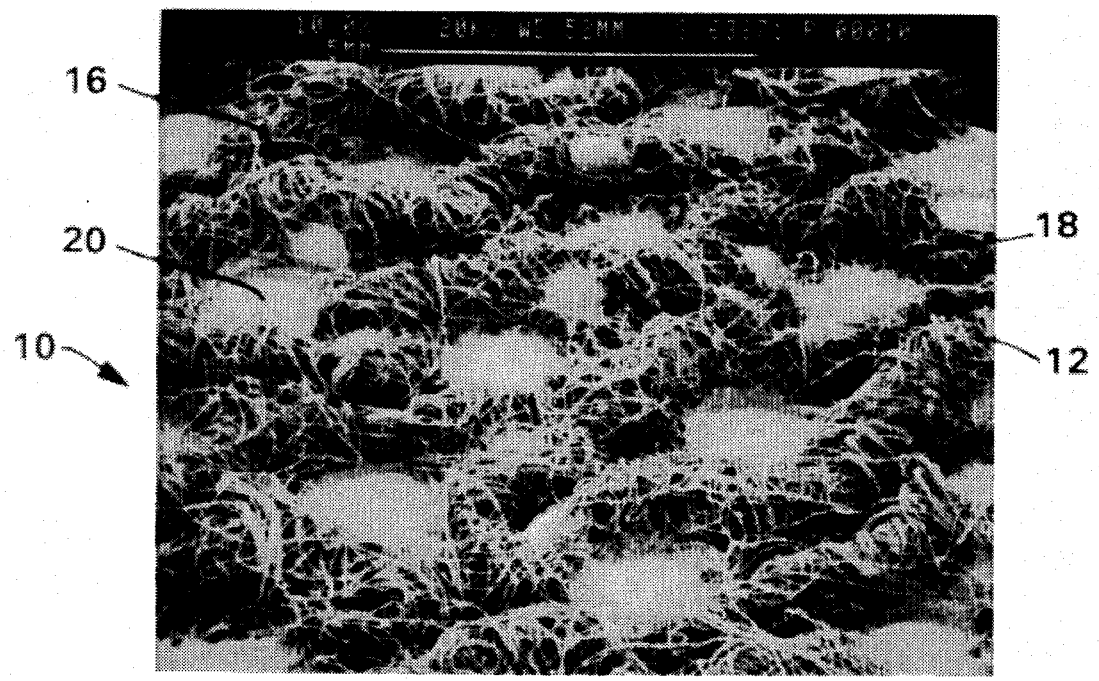
FIG. 5 is a photomicrograph of the creped nonwoven layer of the loop material of the present invention.

As a result of the creping process employed in making the creped nonwoven laminate loop material of this invention, nonwoven layer 12 (see FIGS. 1 and 2) is creped or "bunched," thereby forming raised areas 16 separated by non-raised areas 18 in nonwoven layer 12 and thus imparting rugosities or wrinkles in nonwoven layer 12. Within raised areas 16, hydroentangled nonwoven layer 12 may be physically separated from and/or unbonded to support layer 14. The raised areas 16 have a first, low fiber density and the fibers within the raised areas 16 exhibit a first, high z-directional orientation. As such, the raised areas 16 are intended to receive and engage the hook elements of a complementary hook material, as shown in FIGS. 3 and 4. The non-raised areas 18 have a second, relatively higher fiber density as compared to the raised areas 16 due to compression or compaction of the fibers of nonwoven layer 12 in the non-raised areas and exhibit a second, relatively lower z-directional fiber orientation. The creping imparted to nonwoven layer 12 by the forming process further serves to increase the basis weight of the nonwoven material, as a larger amount of nonwoven material is compacted within a given unit area. The basis weight of the nonwoven material has been observed to increase by as much as a factor of 2, or more, depending, for example, on the degree of creping imparted by the creping apparatus described hereinafter. The creped structure of nonwoven layer 12 provides resistance to compression of the fibrous structure of nonwoven layer 12, thereby facilitating entry and engagement of the hook elements of hook material 22 during use of the hook and loop fastening system. FIG. 5 illustrates in detail the features and contours of nonwoven layer 12.

Support layer 14 can be generally described as any material, including woven or nonwoven materials or thermoplastic films, that can be suitably bonded to an outer surface of the nonwoven layer 12 in order to provide a foundation for the nonwoven layer 12. Support layer 14 can, for example, be formed by the material of an underlying substrate, such as the outer cover or backsheet of an absorbent article. Thus, support layer 14 provides structural integrity to the creped nonwoven laminate material, and serves to dimensionally stabilize the fibers within nonwoven layer 12.

Suitable film formulations used in forming support layer 14 include homopolymers and copolymers of ethylene or propylene, such as low density polyethylene (LDPE), linear low density polyethylene (LLDPE), ethylene/vinyl acetate copolymers (EVA), high density polyethylene (HDPE), or a mixture of two or more of these polymers. Such films may be monolayer or multi-layer and can be formed by any suitable film manufacturing process as is well known in the art, including, for example, blow-molding, cast-extrusion and bioriented-extrusion. For example, in the specific embodiment shown in FIGS. 1 and 2, support layer 14 is a 0.6 mil thick, blow-molded mono-layer film sold under the product designation XBPP-133 by Consolidated Thermoplastics Co., having offices in Dallas, Tex. Based upon nuclear magnetic resonance (NMR) analysis, this film includes 84 percent polypropylene and 16 percent polyethylene, by weight, based upon the total film weight. Other suitable films used in forming support layer 14 can be made of or include a heterophasic polymer composition as described in U.S. Pat. No. 5,368,927 to Lesca et al., or U.S. Pat. No. 5,453,318 to Giacobbe, the disclosures of which are incorporated herein by reference. Typical commercially available thermoplastic film materials have initial thicknesses ranging from about 0.4 mil to about 5 mils.

If support layer 14 is formed of a nonwoven material, such nonwoven layer can be formed by any suitable known process, such as those described hereinabove.

Although in the embodiments shown, support layer 14 is illustrated as coextensive with nonwoven layer 12, the present invention is not limited to such embodiments. For example, nonwoven layer 12 can be creped singly and then secured or attached directly to an underlying substrate, such as an outer cover of an absorbent article. In this alternative embodiment, the substrate functions as a support layer 14. If the outer cover of an absorbent article forms the support layer 14 of the present invention, the outer cover may be formed of any suitable material that provides the required functionality as described herein for support layer 14. By way of example only, a typical material used in forming absorbent article outer covers is polyethylene film.

Figure 7:
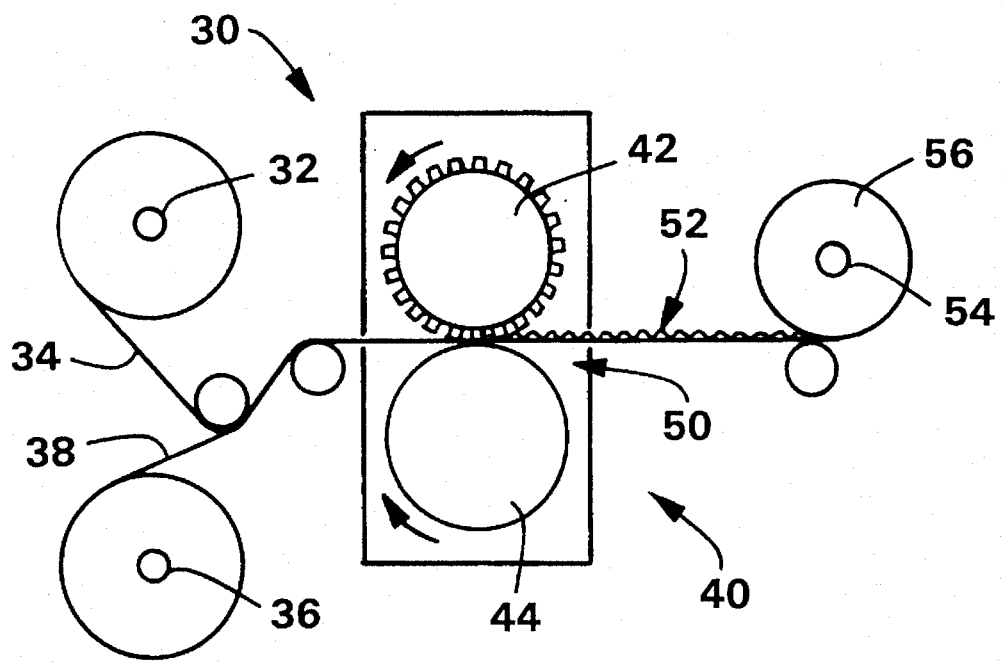
FIG. 7 is a schematic side view of a process and apparatus for making the loop material of the present invention.
Figure 8:
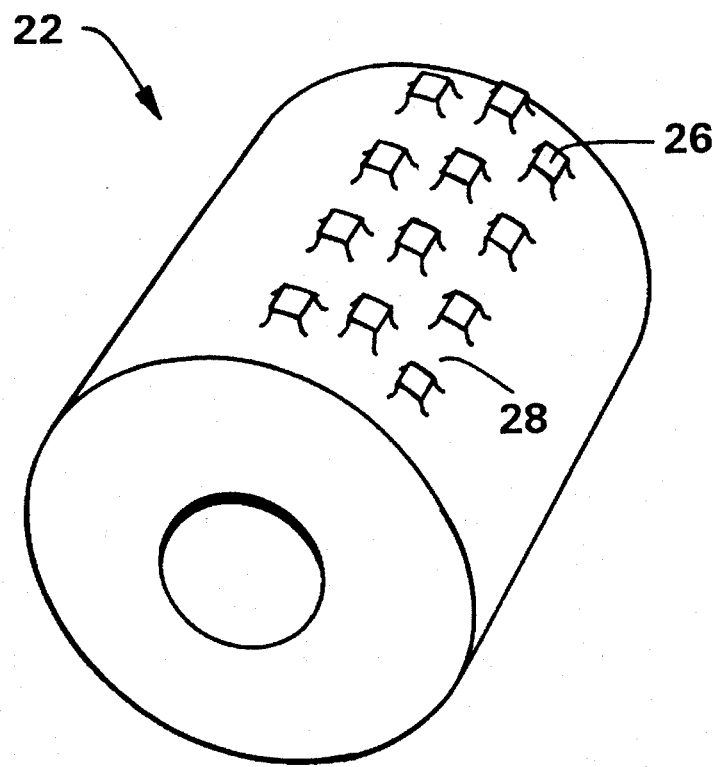
FIG. 8 is a partial perspective view of a pattern roll that can be used in accordance with the process and apparatus of FIG. 7.

Referring now to FIG. 7, a process and apparatus for forming the creped nonwoven laminate loop material of this invention now will be described. A suitable process and apparatus for forming such creped nonwoven laminate materials is described in detail in the commonly assigned U.S. patent application Ser. No. 463,592, filed on Jun. 5, 1995, which is incorporated herein by reference. It should be understood, however, that any process and apparatus suitable for forming a creped nonwoven laminate loop material having the functionality and attributes described herein with respect to Applicants' invention may be employed.

In FIG. 7, apparatus for forming the creped nonwoven laminate loop material of this invention is represented generally as element 30. The apparatus 30 includes a first web unwind 36 for a first web 38 and an optional second web unwind 32 for a second web 34. For purposes of illustration only, the first web unwind 36 shall be described as having a roll of plastic film 38 and the second web unwind 32 shall be described as having a roll of nonwoven web material 34 such as a spunbond, air laid, wet laid or bonded carded web. It should be understood, however, that unwinds 32 and 36 may be used to feed any type of web material into the apparatus shown that is compatible therewith and forms the creped nonwoven laminate loop material of the present invention. It further should be understood that although the apparatus of FIG. 7 shows web unwinds 36 and 32, the creping assembly 30 may be placed in a continuous (in-line) process with the conventional nonwoven forming and/or film forming apparatus described herein.

In order to further manipulate the properties of the creped nonwoven laminate loop material formed by the apparatus depicted in FIG. 7, it has been found advantageous to control the respective rotational speeds of the unwinds 32 and 36. As a result, it is desirable to provide both unwinds with driving and/or braking means (not shown) to control the rotational speeds of the unwinds, as will be explained in further detail below. Such driving and/or braking means are widely known to those of ordinary skill in the art and are commonly used in conjunction with such unwinds to control tension in the web materials being unwound.

First web 38 (or simply "web" if only one unwind is used) is taken off the unwind 36 and second web 34 is taken off second unwind 32. Both webs 34 and 38 are passed into a creping assembly 40 that includes a first or pattern roll 42 and a second or an anvil roll 44, both of which are driven and/or braked with respect to one another so as to create a rotational speed differential between the two rolls 42 and 44. Suitable means for driving the first and second rolls 42 and 44 include, for example, electric motors (not shown).

Pattern roll 42 is a right circular cylinder that may be formed of any suitable, durable material, such as, for example, steel, to reduce the wear on the rolls during use. Pattern roll 42 has a pattern of raised areas 46 separated by a pattern of non-raised or depressed areas 48. The raised areas 46 are designed to form a nip with the smooth or flat outer surface of oppositely positioned anvil roll 44, which also is a right circular cylinder that can be formed of any suitable, durable material. The size, shape and number of raised areas 46 on pattern roll 42 can be varied to meet the particular end-use needs of the creped nonwoven laminate loop material being formed thereby. Likewise, the pattern of raised areas 46 on pattern roll 42 can be continuous or discontinuous, as necessitated by the end use application. Typically the relative percentage of raised areas per unit area of the pattern roll 42 will range between about 5 and about 50 percent and the average contact area of each of the raised areas 46 will range between about 0.20 and about 1.6 square millimeters ($mm^2$). Generally, the height of the raised areas 46 will range from about 0.25 to about 1.1 millimeters (mm), although heights outside of this range can be used for specific applications if so desired. The number of contact areas per unit area of the pattern roll 42 generally will range between about 3 and about 100 raised areas per square centimeter ($cm^2$) of the pattern roll 42. The shape, geometry or footprint of the raised areas 46 on pattern roll 42 also can be varied. Ovals, squares, circles and diamonds are examples of shapes that can be advantageously employed.

The temperature of the outer surface of pattern roll 42 can be varied by heating or cooling relative to anvil roll 44. Heating and/or cooling can affect the features of the web(s) being processed and the degree of bonding of multiple webs being passed through the nip formed between the counter-rotating pattern roll 42 and anvil roll 44. The specific ranges of temperatures to be employed in bonding nonwoven layer 12 to support layer 14 is dependent upon a number of factors, including the types of materials employed in forming nonwoven layer 12 and support layer 14, the inlet or line speed(s) of the layers 12 and 14 passing through the nip formed between pattern roll 42 and anvil roll 44, and the nip pressure between pattern roll 42 and anvil roll 44. Common heating techniques include hot oil and electrical resistance heating, as are well known to those of ordinary skill in the art.

Anvil roll 44 has an outer surface that is much smoother than pattern roll 42, and preferably is smooth or flat. It is possible, however, for anvil roll 44 to have a slight pattern on its outer surface and still be considered smooth or flat for purposes of the present invention. For example, if anvil roll 44 is made from or has a softer surface, such as resin impregnated cotton or rubber, it will develop surface irregularities, yet it will still be considered smooth or flat for purposes of the present invention. Such surfaces are collectively referred to herein as "flat." Anvil roll 44 provides the base for pattern roll 42 and webs of material 12 and 14 to contact and shear against. Typically, anvil roll 44 will be made from steel, or materials such as hardened rubber, resin-treated cotton or polyurethane.

Anvil roll 44 also may have flat areas separated by depressed areas (not shown) so that only select areas of anvil roll 44 will contact raised areas 46 of pattern roll 42. The same technique may be used on pattern roll 42. As a result, creping can be selectively imparted to specific regions of the web being processed. As with pattern roll 42, anvil roll 44 may be heated and/or cooled to further affect the properties of the webs being processed.

Pattern roll 42 and anvil roll 44 are rotated in opposite directions to one another so as to draw the webs of materials 12 and 14 through the nip area defined therebetween. Pattern roll 42 has a first rotational speed measured at its outer surface and anvil roll 44 has a second rotational speed measured at its outer surface, with the second rotational speed of the anvil roll 44 exceeding the first rotational speed of the pattern roll 42. The inlet speeds of the webs 12 and 14 may be adjusted to be less than, equal to or greater than the first rotational speed of pattern roll 42.

The locations of the oppositely positioned two rolls 42 and 44 may be varied to create a nip area 50 between pattern roll 42 and anvil roll 44. The nip pressure within nip area 50 can be varied depending upon the properties of the web itself or webs themselves and the degree of bonding and/or creping desired. Other factors which will allow variances in the nip pressure will include the speed differential between pattern roll 42 and anvil roll 44, the temperature of the rolls 42 and 44 and size and spacing of the raised areas 46. For such materials as films and nonwovens, the nip pressure typically will range between about 2.0 and about 6.0 kilograms per lineal millimeter (kg/lmm). Other nip pressures are possible depending upon the particular end use application desired.

By manipulating the respective rotational speeds of the pattern roll 42 and anvil roll 44 such that the speed of the anvil roll 44 exceeds that of the pattern roll 42, the creped nonwoven laminate loop material of the present invention can be formed. Rotating the anvil roll 44 faster than the pattern roll 42 causes the web of material contacting the pattern roll 42, which is nonwoven layer 12 in FIG. 7, to be creped, compacted or bunched in and around the raised areas 46 of pattern roll 42 as it passes through the nip area 50 formed between the rolls. The web of material contacting the faster rotating anvil roll 44, however, need not be compacted or bunched. Increasing the speed differential between the pattern roll 42 and anvil roll 44 has been observed to increase the amount of crepe in the material being processed. As nonwoven layer 12 and support layer 14 are bonded together or laminated within the nip area 50, raised areas 16 are formed wherein the nonwoven material is bunched to form rugosities in nonwoven layer 12. In the embodiment shown, raised areas 16 encircle bonding points 20 within the non-raised areas 18 of nonwoven layer 12. The degree of creping or bunching will depend not only upon the speed differential of the two rolls, but also upon other processing conditions, including the windup speeds, the respective roll temperatures and the area (spacing and depth) between the raised areas 46. Once the webs 12 and 14 pass through the creping assembly 40, the creped nonwoven laminate loop material 52 formed thereby has features and contours as shown in the photomicrograph of FIG. 5 hereof.

Nonwoven layer 12 and support layer 14 are bonded to one another at a plurality of bond points 20 within the non-raised areas 18 of nonwoven layer 12, thereby forming a plurality of raised areas 16 in nonwoven layer 12 separating the non-raised areas 18. The degree of bonding or attachment between nonwoven layer 12 and support layer 14 should be sufficient to prevent delamination of layers 12 and 14 when subjected to the forces and pressures typically exerted during normal use (i.e., during repeated fastening and removal of the hook elements of a complementary hook material). As noted above, the non-raised areas 18 adjacent the bond points 20 will have an increased fiber density, as compared to the fiber density of the raised areas 16 intermediate non-raised areas 18, resulting from the compression or compaction of the fibers of nonwoven layer 12 imparted by the bonding process described above. In the embodiment shown, bond points 20 are discrete or discontinuous bonded areas encircled by raised areas 16 in which nonwoven layer 12 and support layer 14 are less bonded or unbonded. The term "unbonded" as used herein is meant to refer to the absence of bonds of sufficient strength to withstand the forces typically encountered during ordinary use of the creped nonwoven laminate loop material of the present invention.

Alternatively, nonwoven layer 12 and support layer 14 may be bonded together along a plurality of bond lines within the non-raised areas 18 of nonwoven layer 12, thereby forming a plurality of substantially continuous pleats or corrugations in raised areas 16 in nonwoven layer 12. These pleats or corrugations are oriented in a direction generally perpendicular to the machine direction of travel of nonwoven layer 12. By "generally perpendicular" it is meant that the angle between the longitudinal axis of the corrugations or pleats formed in nonwoven layer 12, or extensions thereof, and the machine direction is between 60° and 120°. As used herein, the term "machine direction" or MD means the length of a material or fabric in the direction in which it is produced (from left to right in FIG. 7). The term "cross machine direction" or CD means the width of a material or fabric, i.e. a direction generally perpendicular to the MD. Such bond lines can be continuous or discontinuous and will be generally parallel to one another. By "generally parallel" it is meant that the bond lines themselves or extensions of the bonds lines will either not intersect, or if they do intersect, the interior angle formed by the intersection will be less than or equal to 30°.

Although bonding or lamination of nonwoven layer 12 and support layer 14 is specifically described herein with reference to heated calender rolls 42 and 44 shown in FIG. 7, any suitable pattern bonding method and apparatus may be employed that achieves sufficient lamination of the two layers 12 and 14. For example, an adhesive bonding process and apparatus as is well known to those of ordinary skill in the art could be utilized to bond layers 12 and 14 together. Alternatively, an ultrasonic bonding process and apparatus as is likewise well known to those of ordinary skill in the art could be used.

As the creped nonwoven laminate loop material 52 exits the creping assembly 40, the loop material 52 is collected on a web take-up winder 54. As with the first unwind 36 and second unwind 32, take-up winder 54 is driven by an electric motor or other drive source which can be varied so as to adjust the speed at which the loop material 52 is wound up into a roll 56. The speed at which the laminate material 52 is wound on the winder 54 will also affect the properties and appearance of the material. Alternatively, take-up winder 54 may be eliminated and laminate material 52 may continue in-line for further processing in web converting apparatus (not shown), such as, for example, application onto an outer cover or backsheet of a personal care absorbent article.

Both the inlet speed of the webs 12 and 14 and the withdrawal speed of the laminate material 52 can be varied to change of the conditions of the process. For example, the inlet speed of webs 12 and 14 can be equal to or greater than the rotational speed of first or pattern roll 42, and equal to or slower than the rotational speed of the second or anvil roll 44. Exiting the nip area 50 formed by pattern roll 42 and anvil roll 44, laminate material 52 can have a withdrawal speed which is equal to or greater than the rotational speed of pattern roll 42, and slower or equal to the rotational speed of anvil roll 44. It is considered advisable, however, to adjust the withdrawal speed of the laminate material 52 such that stretching of the material 52 is limited, or avoided entirely, in order to maintain the 3-dimensional surface topography of the material 52, and particularly the z-directional orientation of fibers within the raised areas 16.

Figure 6:
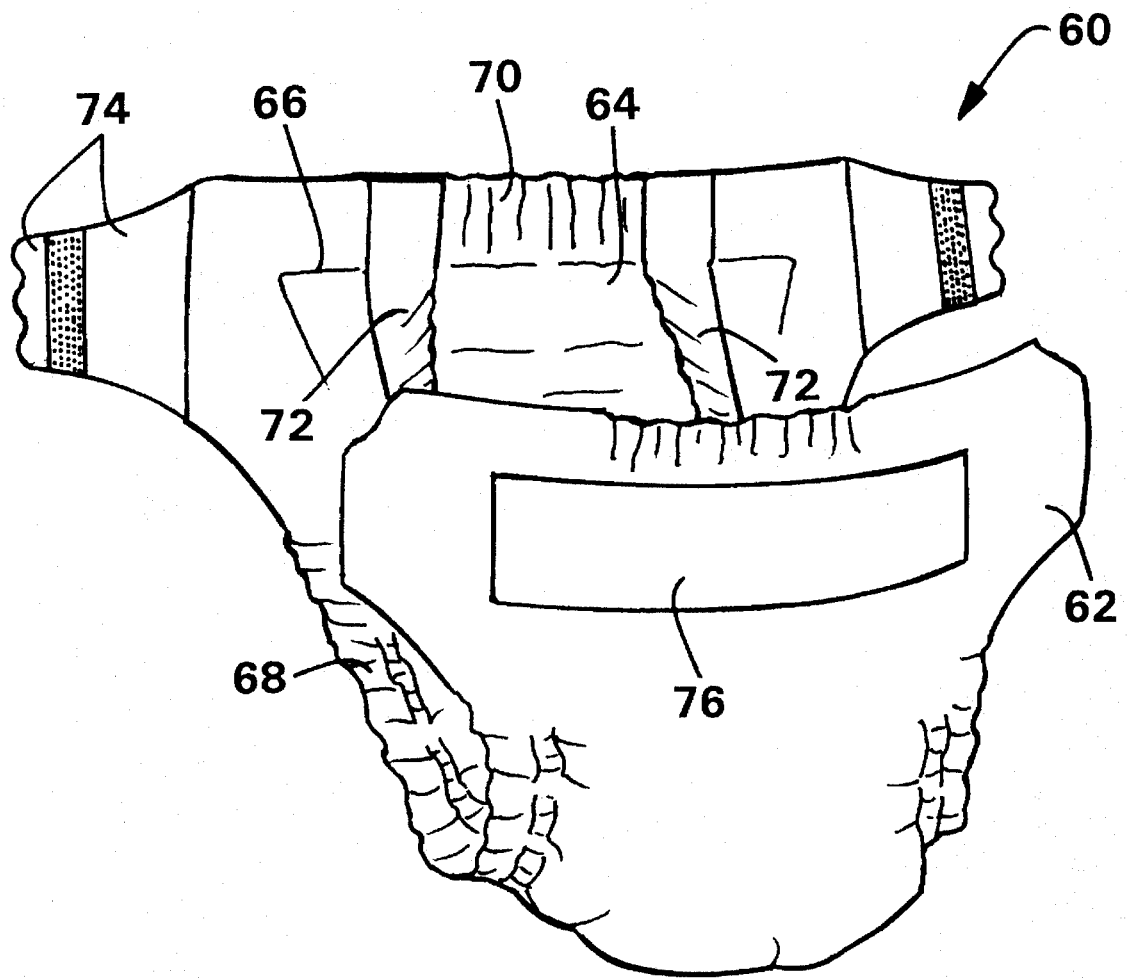
FIG. 6 is a perspective view of a disposable diaper with the loop material of the present invention as a loop patch.

Once the creped nonwoven laminate loop material of the present invention is formed, it can be attached to the outer cover or backsheet of a personal care absorbent article, such as disposable diaper 60 shown in FIG. 6. More specifically, the exposed surface of support layer 14 opposite the surface attached to creped nonwoven layer 12 can be secured to outer cover 62 of diaper 60 by known attachment means, including adhesives, thermal bonding, ultrasonic bonding or a combination of such means. A wide variety of adhesives can be employed, including, but not limited to, solvent-based, water-based, hot-melt and pressure sensitive adhesives. Powdered adhesive can also be applied to the materials and then heated to activate the powder adhesive and perfect bonding.

Diaper 60, as is typical for most personal care absorbent articles, includes a liquid permeable body side liner 64 and a liquid impermeable outer cover 62. Various woven or nonwoven fabrics can be used for body side liner 64. For example, the body side liner may be composed of a meltblown or spunbond nonwoven web of polyolefin fibers, or a bonded carded web of natural and/or synthetic fibers. Outer cover 62 is typically formed of a thin thermoplastic film, such as polyethylene film. The polymer film outer cover may be embossed and/or matte finished to provide a more aesthetically pleasing appearance. Other alternative constructions for outer cover 62 include woven or nonwoven fibrous webs that have been constructed or treated to impart the desired level of liquid impermeability, or laminates formed of a woven or nonwoven fabric and thermoplastic film. Outer cover 62 may optionally be composed of a vapor or gas permeable, "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability.

Disposed between liner 64 and outer cover 62 is an absorbent core 66 formed, for example, of a blend of hydrophilic cellulosic woodpulp fluff fibers and highly absorbent gelling particles (e.g., superabsorbent). Absorbent core 66 is generally compressible, conformable, non-irritating to the wearer's skin, and capable of absorbing and retaining liquid body exudates. For purposes of this invention, absorbent core 66 can comprise a single, integral piece of material, or a plurality of individual separate pieces of material. The size and absorbent capacity of absorbent core 66 should be compatible with the size of the intended user and the liquid loading imparted by the intended use of the diaper 60.

Elastic members may optionally be disposed adjacent each longitudinal edge 68 of diaper 60. Such elastic members are arranged to draw and hold the lateral, side margins 68 of diaper 60 against the legs of the wearer. Additionally, elastic members also may be disposed adjacent either or both of the end edges 70 of diaper 60 to provide an elasticized waistband.

Diaper 60 may further include optional containment flaps 72 made from or attached to body side liner 64. Suitable constructions and arrangements for such containment flaps are described, for example, in U.S. Pat. No. 4,704,116, to K. Enloe, the disclosure of which is incorporated herein by reference in its entirety.

To secure the diaper 60 about the wearer, the diaper will have some type of fastening means attached thereto. As shown in FIG. 6, the fastening means is a hook and loop fastening system including hook elements 74 attached to the inner and/or outer surface of outer cover 62 in the back waistband region of diaper 60 and one or more loop elements or patches 76 made from the loop material of the present invention attached to the outer surface of outer cover 62 in the front waistband region of diaper 60.

Having described the above embodiments of the present invention, a series of sample creped nonwoven laminate loop materials were formed to further illustrate the present invention. These samples were tested to determine peel strength, shear strength, and the degree of attachment (lamination) between the creped nonwoven layer and support layer.

The peel strength of a loop material is a gauge of its functionality. More specifically, peel strength is a term used to describe the amount of force needed to pull apart the male and female components of a hook and loop fastening system. One way to measure the peel strength is to pull one component from the other at a 180 degree angle.

Shear strength is another measure of the strength of a hook and loop fastening system. Shear strength is measured by engaging the male and female components and exerting a force along the plane defined by the connected surfaces in an effort to separate the two components.

The degree of attachment or lamination between the creped nonwoven layer and support layer of the creped nonwoven laminate loop material of the present invention is another gauge of its functionality. Delamination refers to the separation of the layers of a laminate material when the bonding mechanism fails. Bond strength is a measure of the average peel force required to separate the component layers of a laminate material.

The test methods used to evaluate individual samples of the creped nonwoven laminate loop material of the present invention are set forth below.

TEST METHODS

Basis Weight

The basis weights of various materials described herein were determined in accordance with Federal Test Method No. 191A/5041. Sample size for the sample materials was 15.24×15.24 centimeters and three values were obtained for each material and then averaged. The values reported below are for the average.

180° Peel Strength Test

The 180° peel strength test involves attaching a hook material to a loop material of a hook and loop fastening system and then peeling the hook material from the loop material at a 180° angle. The maximum load needed to disengage the two materials is recorded in grams.

To perform the test, a continuous rate of extension tensile tester with a 5000 gram full scale load is required, such as a Sintech System 2 Computer Integrated Testing System available from Sintech, Inc., having offices in Research Triangle Park, N.C. A 75 mm by 102 mm sample of the loop material is placed on a flat, adhesive support surface. A 45 mm by 12.5 mm sample of hook material, which is adhesively and ultrasonically secured to a substantially inelastic, nonwoven material, is positioned over and applied to the upper surface of the loop material sample. To ensure adequate and uniform engagement of the hook material to the loop material, a 4½ pound hand roller is rolled over the combined hook and loop materials for one cycle, with one cycle equaling a forward and a backward stroke of the hand roller. One end of the fingertab material supporting the hook material is secured within the upper jaw of the tensile tester, while the end of the loop material directed toward the upper jaw is folded downward and secured within the lower jaw of the tensile tester. The placement of the respective materials within the jaws of the tensile tester should be adjusted such that minimal slack exists in the respective materials prior to activation of the tensile tester. The hook elements of the hook material are oriented in a direction generally perpendicular to the intended directions of movement of the tensile tester jaws. The tensile tester is activated at a crosshead speed of 500 mm per minute and the peak load in grams to disengage the hook material from the loop material at a 180° angle is then recorded.

Dynamic Shear Strength Test

The dynamic shear strength test involves engaging a hook material to a loop material of a hook and loop fastening system and then pulling the hook material across the loop material's surface. The maximum load required to disengage the hook from the loop is measured in grams.

To conduct this test, a continuous rate of extension tensile tester with a 5000 gram full scale load is required, such as a Sintech System 2 Computer Integrated Testing System. A 75 mm by 102 mm sample of the loop material is placed on a flat, adhesive support surface. A 45 mm by 12.5 mm sample of hook material, which is adhesively and ultrasonically secured to a substantially inelastic, nonwoven material, is positioned over and applied to the upper surface of the loop material sample. To ensure adequate and uniform engagement of the hook material to the loop material, a 4½ pound hand roller is rolled over the combined hook and loop materials for five cycles, with one cycle equaling a forward and a backward stroke of the hand roller. One end of the nonwoven material supporting the hook material is secured within the upper jaw of the tensile tester, and the end of the loop material directed toward the lower jaw is secured within the lower jaw of the tensile tester. The placement of the respective materials within the jaws of the tensile tester should be adjusted such that minimal slack exists in the respective materials prior to activation of the tensile tester. The hook elements of the hook material are oriented in a direction generally perpendicular to the intended directions of movement of the tensile tester jaws. The tensile tester is activated at a crosshead speed of 250 mm per minute and the peak load in grams to disengage the hook material from the loop material is then recorded.

Bond Strength Test

To test the bond strength between the creped nonwoven layer and support layer, a delamination or bond strength test is performed. Samples of the creped nonwoven laminate loop material measuring 102 mm by 152 mm are cut and manually separated at one end for a distance of about 55 mm to produce edges that can be placed within the jaws of a Sintech System 2 Computer Integrated Testing System. The free end of the nonwoven layer is secured in the moving, upper jaw, while the free end of the support layer is secured in the stationery, lower jaw. The jaw gap is set at a span of 100 millimeters and enough of the loop material is left in the laminated state so that the jaws can travel 65 millimeters. The sample is positioned in the jaws so that the sample will start delaminating before the jaws expand 10 millimeters. The crosshead speed is set at 300 millimeters per minute and the average peel strength in grams to delaminate the nonwoven layer from the support layer is then recorded as the bond strength.

EXAMPLES

A total of 18 examples are set forth below. In all of the examples, the support layer was a blown thermoplastic film. The film composition included, on a weight percent basis based upon the total weight of the film, about 84 percent polypropylene and about 16 percent polyethylene, according to NMR analysis. The film had a thickness or bulk of 0.6 mil. This film is sold under the product designation XBPP-133 by Consolidated Thermoplastics Co.

The samples of the creped nonwoven laminate loop material all were formed using a creping process and apparatus, as described herein. The nonwoven layer and film support layer were passed through the nip formed between two counter-rotating thermal bonding rolls including a pattern roll and an anvil roll. The nonwoven layer was positioned adjacent to and in contact with the pattern roll, while the film support layer was positioned adjacent to and in contact with the anvil roll. The pattern roll was heated to a temperature of about 127° C. and the anvil roll was heated to a temperature of about 116° C. Both rolls were heated using an internal hot oil system. The nip pressure along the interface between the pattern roll and the anvil roll was about 65.7 pounds per lineal inch (pli) (about 1.17 kilograms per lineal millimeter (kg/lmm)). As a result of the nonwoven layer and film support layer passing through the creping assembly, a creped nonwoven laminate loop material was formed in accordance with the teachings herein.

EXAMPLES 1–7

In these examples, the nonwoven web was formed of melt-spun filaments made using a pilot-scale apparatus, essentially as described in U.S. Pat. No. 3,802,817 to Matsuki et al. The melt-spun filaments were formed from an extrudable thermoplastic resin of a random copolymer of propylene and ethylene containing, on a weight percent basis based upon the total weight of the resin, about 5.5 percent ethylene and about 94.5 percent propylene, obtained from Shell Oil Company, having offices in Houston, Tex., under the product designation WRD6277. The melt-spun filaments were essentially continuous in nature and had an average fiber size of 2–3 dpf. The spunbond nonwoven web had a percent bond area of about 10% and a basis weight of about 23.6 grams per square meter (gsm). The spunbond nonwoven web and film support layer were formed into a creped nonwoven laminate loop material using the creping assembly described herein. The inlet speed of the nonwoven web into the nip formed between the pattern roll and anvil roll was about 11.0 meters per minute (m/min.). The pattern roll had a rotational speed of about 6.1 m/min. and the anvil roll had a rotational speed of about 18.3 m/min., resulting in a pattern roll/anvil roll speed differential of about 3:1.

EXAMPLE 8

The creped nonwoven laminate loop material of this example was formed under the same process conditions and using the same melt-spun filaments described above for Examples 1–7 except as follows:

In this example, the inlet speed of the nonwoven web into the nip formed between the pattern roll and anvil roll was about 16.5 meters per minute (m/min.). The pattern roll had a rotational speed of about 9.1 m/min. and the anvil roll had a rotational speed of about 18.3 m/min., resulting in a pattern roll/anvil roll speed differential of about 2:1.

EXAMPLE 9

The creped nonwoven laminate loop material of this example was formed under the same process conditions and using the same melt-spun filaments described above for Examples 1–7 except as follows:

In this example, the nonwoven web had a basis weight of about 16.9 gsm.

EXAMPLES 10

The creped nonwoven laminate loop material of this example was formed under the same process conditions and using the same melt-spun filaments described above for Example 8 except as follows:

In this example, the nonwoven web had a basis weight of about 16.9 gsm.

EXAMPLE 11

In this example, the nonwoven web was formed of melt-spun filaments formed from an extrudable thermoplastic resin of a random copolymer of propylene and ethylene containing, on a weight percent basis based upon the total weight of the resin, about 3.0 percent ethylene and about 97.0 percent propylene, obtained from Exxon Corp., having offices in Houston, Tex., under the product designation 9355. The melt-spun filaments were essentially continuous in nature and had an average fiber size of 2–3 dpf. The spunbond nonwoven web had a percent bond area of about 10% and a basis weight of about 23.6 grams per square meter. The inlet speed of the nonwoven web into the nip formed between the pattern roll and anvil roll was about 16.5 meters per minute (m/min.). The pattern roll had a rotational speed of about 9.1 m/min. and the anvil roll had a rotational speed of about 18.3 m/min., resulting in a pattern roll/anvil roll speed differential of about 2:1.

EXAMPLE 12

The creped nonwoven laminate loop material of this example was formed under the same process conditions and using the same melt-spun filaments described above for Example 11 except as follows:

In this example, the basis weight of the nonwoven web was about 16.9 gsm.

EXAMPLE 13

The creped nonwoven laminate loop material of this example was formed under the same process conditions and using the same melt-spun filaments described above for Example 11 except as follows:

In this example, the inlet speed of the nonwoven web into the nip formed between the pattern roll and anvil roll was about 11.0 meters per minute (m/min.). The pattern roll had a rotational speed of about 6.1 m/min. and the anvil roll had a rotational speed of about 18.3 m/min., resulting in a pattern roll/anvil roll speed differential of about 3:1.

EXAMPLE 14

The creped nonwoven laminate loop material of this example was formed under the same process conditions and using the same melt-spun filaments described above for Example 13 except as follows:

In this example, the basis weight of the nonwoven web was about 16.9 gsm.

EXAMPLE 15

The creped nonwoven laminate loop material of this example was formed under the same process conditions and using the same melt-spun filaments described above for Example 12 except as follows:

In this example, the nonwoven web had a percent bond area of about 15%.

EXAMPLE 16

The creped nonwoven laminate loop material of this example was formed under the same process conditions and using the same melt-spun filaments described above for Example 14 except as follows:

In this example, the nonwoven web had a percent bond area of about 15%.

EXAMPLE 17

The creped nonwoven laminate loop material of this example was formed under the same process conditions and using the same melt-spun filaments described above for Example 13 except as follows:

In this example, the nonwoven web had a percent bond area of about 15%.

EXAMPLE 18

The creped nonwoven laminate loop material of this example was formed under the same process conditions and using the same melt-spun filaments described above for Example 11 except as follows:

In this example, the nonwoven web had a percent bond area of about 15%.

The above-described sample materials had the following properties:

TABLE I

| EXAMPLE NO. | Attachment Strength (grams) n = 3** | Peel Strength (grams) n = 4 | Shear Strength (grams) n = 4 |
| --- | --- | --- | --- |
| 1 | 1425 | 517 | 3529 |
| 2 | 1483 | 711 | 3805 |
| 3 | 1110 | 590 | 3188 |
| 4 | 894 | 518 | 3300 |
| 5 | 2477 | 483 | 3454 |
| 6 | 2039 | 405 | 3511 |
| 7 | 2410 | 419 | 2635 |
| 8 | 888 | 546 | 2695 |
| 9 | N/A* | 504 | 3421 |

TABLE I-continued

| EXAMPLE NO. | Attachment Strength (grams) n = 3** | Peel Strength (grams) n = 4 | Shear Strength (grams) n = 4 |
| --- | --- | --- | --- |
| 10 | N/A | 365 | 3128 |
| 11 | 940 | 504 | 3540 |
| 12 | 1226 | 421 | 2646 |
| 13 | 1754 | 627 | 3356 |
| 14 | N/A | 518 | 3487 |
| 15 | 1164 | 246 | 2720 |
| 16 | 1190 | 313 | 2526 |
| 17 | 1130 | 234 | 2638 |
| 18 | 1153 | 239 | 2884 |

*N/A - Indicates spunbond nonwoven layer could not be manually separated from film support layer.
**The values indicated in Table I above are average values, based upon n measurements performed on each sample material described in Examples 1–18.

For certain of the above-described Examples, the basis weight of the sample laminate material, and the nonwoven and film support layers after lamination, were measured.

TABLE II

| EXAMPLE NO. | LAMINATE BASIS WEIGHT (gsm) n = 5 | NONWOVEN BASIS WEIGHT (gsm) n = 5 | FILM BASIS WEIGHT (gsm) n = 5 |
| --- | --- | --- | --- |
| 7 | 78.2 | 47.6 | 17.0 |
| 8 | 54.4 | 37.4 | 17.0 |
| 9 | 61.2 | N/A | N/A |
| 10 | 47.6 | N/A | N/A |
| 11 | 57.8 | 37.4 | 20.4 |
| 12 | 51.0 | 27.2 | 23.8 |
| 13 | 78.2 | 44.2 | 34.0 |
| 14 | 64.6 | 32.3 | 30.6 |

Although specific values for attachment, peel and shear strength were provided for the above-described examples, the creped nonwoven laminate loop material of the present invention should not be limited to such values. Generally, the creped nonwoven laminate loop material should have a combination of attachment, peel and shear strength that is suitable for its intended end use application. More specifically, in order to avoid delamination of the nonwoven and support layers during use, the attachment strength should exceed about 500 grams, or suitably exceed about 800 grams. Peel strengths in the range of from about 200 grams to about 800 grams, or higher, are considered suitable for use in the present invention. Likewise, shear strengths ranging from about 2300 grams to about 4200 grams, or higher, are considered suitable for use in the present invention. Likewise, the total basis weight of the creped nonwoven laminate loop material may be adapted to suit its intended end use application. Total basis weights in the range of from about 34 grams per square meter to about 85 grams per square meter, and more particularly in the range of from about 44 grams per square meter to about 75 grams per square meter, are considered suitable for use in the present invention.

It is contemplated that the creped nonwoven laminate loop material constructed in accordance with the present invention will be tailored and adjusted by those of ordinary skill in the art to accommodate various levels of performance demand imparted during actual use. Accordingly, while this invention has been described by reference to the above embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

We claim:

1. A creped nonwoven laminate loop material comprising:

a nonwoven layer having a percent bond area of between about 10 percent and about 25 percent;

said nonwoven layer having a plurality of raised areas separated by a plurality of non-raised areas;

said raised areas of said nonwoven layer having a first fiber density and first z-directional fiber orientation and said non-raised of said nonwoven layer having a second fiber density and second z-directional fiber orientation, said first fiber density being less than said second fiber density and said first z-directional fiber orientation being greater than said second z-directional fiber orientation; and a support layer;

said nonwoven layer and said support layer being bonded together at a plurality of bond points within said non-raised areas.

2. A loop material according to claim 1 wherein said nonwoven layer has a percent bond area of between about 13 percent and about 20 percent.

3. A loop material according to claim 2 wherein said nonwoven layer has a percent bond area of between about 15 percent and about 18 percent.

4. A loop material according to claim 1 wherein said nonwoven layer is a spunbond web.

5. A loop material according to claim 1 wherein said nonwoven layer is a bonded carded web.

6. A loop material according to claim 1 wherein said nonwoven layer is an airlaid web.

7. A loop material according to claim 1 wherein said support layer is a nonwoven web.

8. A loop material according to claim 1 wherein said support layer is a film.

9. A loop material according to claim 1 wherein said nonwoven layer comprises a polyolefin.

10. A loop material according to claim 9 wherein said nonwoven layer comprises a random copolymer containing from about 0.5 percent to about 10 percent, by weight, ethylene, and from about 99.5 to about 90 percent, by weight, propylene.

11. A loop material according to claim 1 wherein said nonwoven layer and said support layer are bonded together along a plurality of continuous bond lines.

12. A loop material according to claim 11 wherein said bond lines are discontinuous.

13. A loop material according to claim 1 having an attachment strength of between about 500 grams and about 2700 grams.

14. A loop material according to claim 1 having a peel strength of between about 200 grams and about 800 grams.

15. A loop material according to claim 1 having a shear strength of between about 2300 grams and about 4200 grams.

16. A loop material according to claim 1 having a total basis weight of between about 34 grams per square meter and about 85 grams per square meter.

17. A loop material according to claim 16 having a total basis weight of between about 44 grams per square meter and about 75 grams per square meter.

18. A loop material according to claim 1 wherein said nonwoven layer and said support layer are thermally bonded.

19. A disposable article comprising:

a bodyside liner;

an outer cover;

an absorbent structure disposed between said liner and said outer cover;

a mechanical fastening system comprising:

a mechanical fastening tab joined to said article, said fastening tab including a male component; and a female component joined to said outer cover and adapted for releasable engagement with said male component;

said female component comprising said loop material of claim 1.

20. A disposable article comprising:

a bodyside liner, an outer cover comprising said loop material of claim 1;

an absorbent structure disposed between said liner and said outer cover;

a mechanical fastening tab joined to said article, said fastening tab including a male component adapted for releasable engagement with said nonwoven layer of said outer cover.

* * * * *